(12) United States Patent
Peters et al.

(10) Patent No.: US 9,498,197 B2
(45) Date of Patent: Nov. 22, 2016

(54) SURGICAL IMPLANT

(71) Applicant: Johhnson & Johnson Medical GmbH, Somerville, NJ (US)

(72) Inventors: Burkhard Peters, Wattenbek (DE); Aida Astani-Matthies, Kaltenkirchen (DE); Christoph Walther, Kattendorf (DE); Thorsten Deichmann, Aachen (DE); Dajana Kaiser, Hamburg (DE); Birgit Hartkop, Berkenthin (DE); Andrea Hennemann, Sievershutten (DE)

(73) Assignee: Johnson & Johnson Medical GMBH, Norderstedt (DE)

(*) Notice: Subject to any disclaimer, the term of this patent is extended or adjusted under 35 U.S.C. 154(b) by 176 days.

(21) Appl. No.: 14/233,021

(22) PCT Filed: Aug. 6, 2013

(86) PCT No.: PCT/EP2013/002356
§ 371 (c)(1),
(2) Date: Jan. 15, 2014

(87) PCT Pub. No.: WO2014/026745
PCT Pub. Date: Feb. 20, 2014

(65) Prior Publication Data
US 2015/0351887 A1    Dec. 10, 2015

(30) Foreign Application Priority Data

Aug. 14, 2012  (DE) .................. 10 2012 016 090

(51) Int. Cl.
*A61B 17/00* (2006.01)
*A61F 2/00* (2006.01)

(52) U.S. Cl.
CPC ......... *A61B 17/0057* (2013.01); *A61F 2/0063* (2013.01); *A61B 2017/00654* (2013.01); *A61F 2230/0067* (2013.01)

(58) Field of Classification Search
CPC ................ A61B 17/0057; A61B 2017/00654; A61B 2017/00601; A61F 2/0063; A61F 2002/0068; A61F 2002/0072; A61F 2230/0067; Y10T 428/23264; Y10T 428/24264
USPC ..................... 600/37; 606/151, 213
See application file for complete search history.

(56) References Cited

U.S. PATENT DOCUMENTS 4,347,847 A * 9/1982 Usher .................. A61F 2/0063
                                                128/898
5,356,432 A * 10/1994 Rutkow ............. A61B 17/0057
                                                600/37

(Continued)

FOREIGN PATENT DOCUMENTS

| CN | 101112335 | 1/2008 |
|----|-----------|--------|
| EP | 0614650 A2 | 2/1994 |
| EP | 0888756 A2 | 6/1998 |
| WO | WO 9745068 A1 | 12/1997 |

OTHER PUBLICATIONS

Hectanooga1. "Paper Cone Angels." YouTube. YouTube, Dec. 13, 2011. Web. Aug. 18, 2016.*

*Primary Examiner* — Eduardo C Robert
*Assistant Examiner* — Charles Wei
(74) *Attorney, Agent, or Firm* — E. Richard Skula

(57) ABSTRACT

A surgical implant (1) adapted for repairing a tissue or muscle wall defect comprises an outer section (8) and an inner section (6) located in the outer section (8), wherein the outer section (8) and the inner section (6) are formed from one double-sheet of a flexible basic structure, which preferably comprises a mesh. The implant can be strengthened by reinforcement elements (12).

14 Claims, 3 Drawing Sheets

(56) References Cited

U.S. PATENT DOCUMENTS

| | | | | |
|---|---|---|---|---|
| 5,716,408 A * | 2/1998 | Eldridge | ............ | A61B 17/0057 606/213 |
| 5,725,577 A * | 3/1998 | Saxon | ................ | A61B 17/0057 606/151 |
| 2003/0181988 A1 * | 9/2003 | Rousseau | .............. | A61F 2/0063 623/23.72 |
| 2012/0010636 A1 * | 1/2012 | Boey | ..................... | A61F 2/0063 606/151 |
| 2012/0310260 A1 * | 12/2012 | Hamlin | ................. | A61F 2/0063 606/151 |

* cited by examiner

Figure 4:
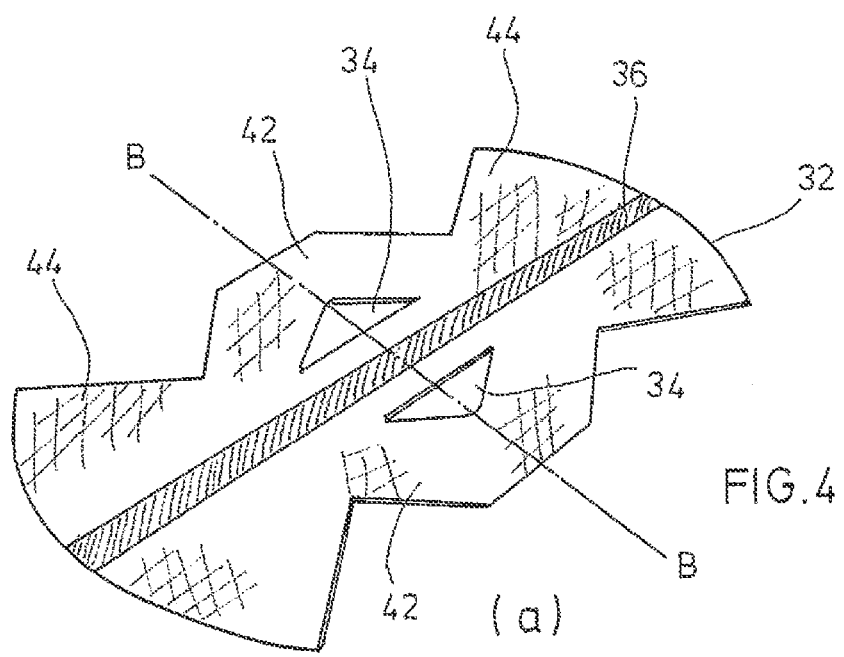

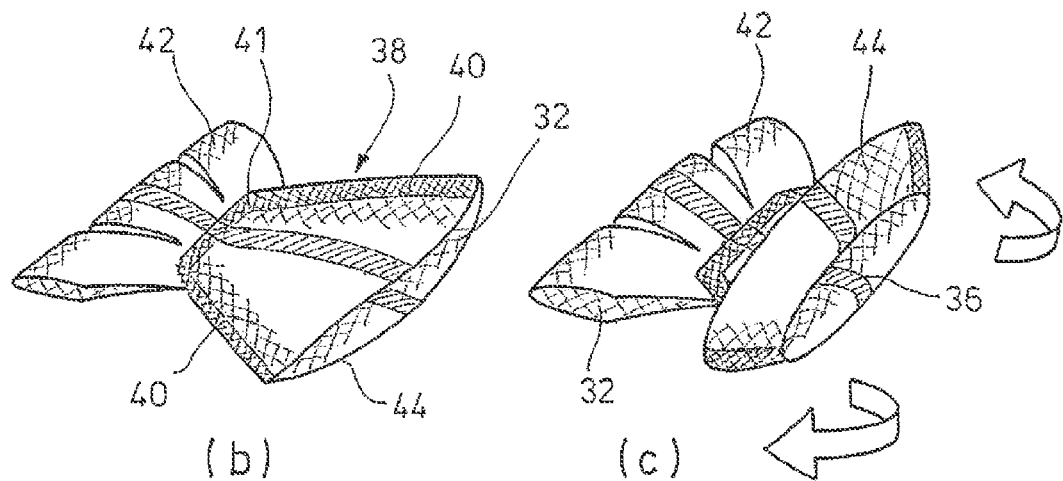
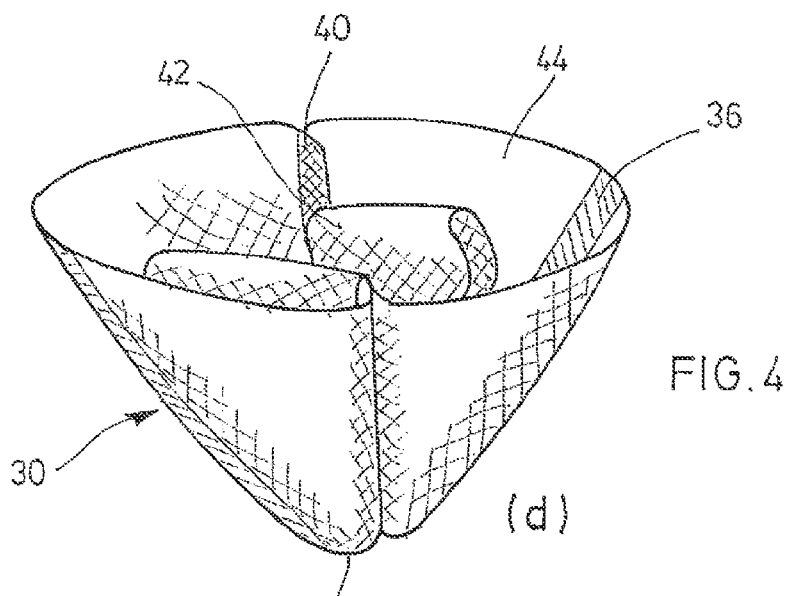
FIG. 4
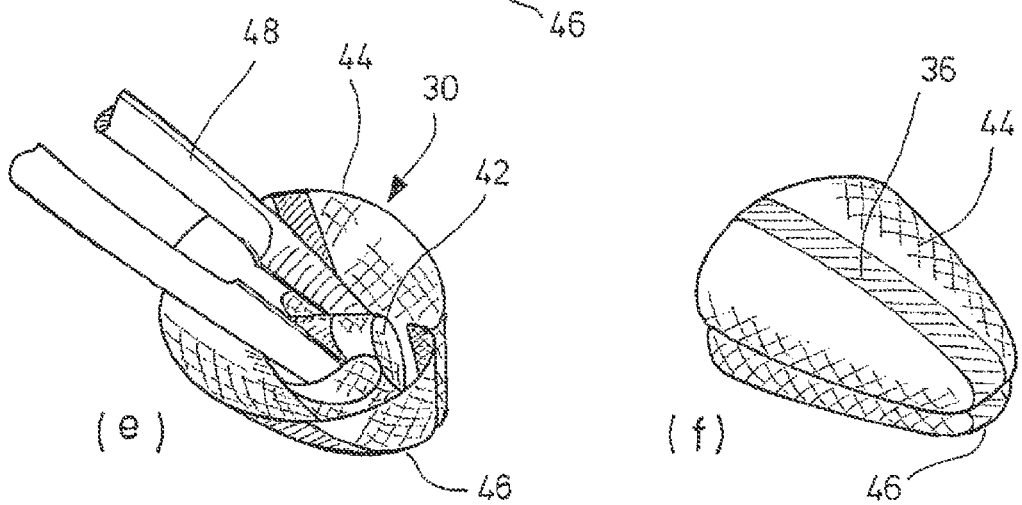

SURGICAL IMPLANT

CROSS REFERENCE TO RELATED APPLICATIONS

This application is the national stage of PCT Application No. PCT/EP2013/002356 filed Aug. 6, 2013 which claims priority to German Application DE 102012016090.9 filed Aug. 14, 2012, the disclosure of which is hereby incorporated by reference in its entirety.

The invention relates to a surgical implant adapted for repairing a tissue or muscle wall defect, in particular for repairing an inguinal hernia, and to a method of manufacturing such implant.

The repair of inguinal hernias is one of the most commonly performed surgical procedures. Various prosthetic materials, typically porous to allow for tissue in-growth, have been provided in a variety of combinations, forms and shapes. The repair of inguinal hernias is often achieved by implanting a mesh plug into the hernia defect. Various materials have been discussed for use as prosthetic plugs. Polypropylene is most often used in the form of a knitted mesh fabric to create the desired shapes.

Many of the commercially available plugs comprise an outer shell (usually made of mesh material) with a separate "filler" material attached to the inside of the outer shell. The filler serves as a means to grasp and position the plug during a surgical procedure. Moreover, the filler, in conjunction with the outer shell, enables tissue in-growth to occur over time.

EP 0 614 650 A2 discloses an implantable prosthesis for muscle or tissue wall repairs comprising a mesh of knitted polypropylene monofilaments. An outer shell made from the mesh material is cone-like (and fluted). Moreover, multiple inner layers of mesh material are provided, which are located in the outer shell and attached in the tip area of the cone configuration. A similar implant is known from WO 97/45068 A1.

CN 101112335 A describes an embeddable multipurpose external hernia remedying slice comprising a substrate and a plurality of petals arranged on the upper surface of the substrate. The distal ends of the petals are free, whereas the proximal ends are fixed to the center of the substrate. A plurality of reinforcement ribs can be arranged on the upper surface of the substrate.

EP 0 888 756 A2 discloses a surgical implant for hernioplasty made of polypropylene mesh material, in which an areal base and a protrusion serving as a plug are joined by stitches.

Separate fabrication steps are required to attach the filler to the inside of the outer shell. Eliminating the filler material would be one way to simplify the manufacture; however, this would also eliminate the benefits and functionality of having a filler material.

It is the object of the invention to provide a surgical implant adapted for repairing a tissue or muscle wall defect, which has the advantages of the prior art implants discussed before, but which can be manufactured in an easier and less expensive way.

This object is achieved by a surgical implant having the features of claim 1. Advantageous versions of the implant follow from the dependent claims.

The surgical implant according to the invention is adapted for repairing a tissue or muscle wall defect, in particular an inguinal hernia. The implant (implantable prosthesis, plug) comprises an outer section and an inner section located in the outer section. The outer section corresponds to the outer shell and the inner section to the filler of the prior art implants discussed above. Thus, the outer section fits into the defect to be repaired, while the inner section serves as a means to grasp and position the implant during a surgical procedure and facilitates tissue in-growth. According to the invention, the outer section and the inner section are formed from one double-sheet of a flexible basic structure. That means, the implant comprises a basic structure which is flexible and, before shaping the implant during the manufacturing process, areal or sheet-like. In the manufacturing process, one double-sheet of the basic structure is provided, in particular by folding a single-sheet (in the following simply called sheet) about a fold line or, analogously, by overlaying two single-sheets. Thus, both the outer section and the inner section are formed from the same double-sheet of material so that it is not required to attach the inner section to the outer section in a separate step. This facilitates the manufacturing process and saves costs. It is not excluded, however, that the implant comprises components or parts in addition to the outer section and the inner section considered so far.

In advantageous versions of the invention, the outer section of the implant has a generally tapered form, e.g. a form generally resembling a cone or a frustum of a cone, which may involve folds or a fluted surface. Such forms include an open base side so that the inner section of the implant is accessible via this open base side.

In a particular advantageous embodiment of the invention, the double-sheet of the basic structure is a single-sheet of the basic structure folded about a fold line or, analogously, is an overlay of two single-sheets of the basic structure, resulting in two opposite sheet parts defining the inner section in an area adjacent to the fold line and the outer section in an area distant from the fold line. The two opposite sheet parts have edge areas facing each other. Preferably, the sheet of the basic structure is symmetric, and the fold line is an axis of symmetry of the sheet (wherein the sheet may also include another axis of symmetry perpendicular to the fold line). In the outer section, at least part of the edge areas facing each other are connected to each other, e.g. by welding, suturing, and/or gluing. Other areas of the two opposite sheet parts facing each other can be connected to each other as well. Such connection areas may also serve as strengthening, stiffening or reinforcement zones. Moreover, in the outer section, the double-sheet of the basic structure is inverted so that the outer section accommodates the inner section. This shape might be understood in an easier way when considering the steps in the manufacturing process, which is described further below in detail.

Preferably, the shape of the sheet material of the basic structure from which the outer section and the inner section are formed is largely optimized to the final three-dimensional shape of the implant. For example, when the sheet is folded about the fold line, the two opposite sheet parts may have lateral cut-outs in a transition region between the inner section and the outer section so that the inner section and the outer section are already well distinct before the inverting step, which facilitates the inverting step.

The inner section of the implant should be accommodated in the outer section. To this end, in the inner section, the double-sheet of the basic structure may include additional folds so that it fits well into the outer section, for example in an accordion-folded manner. Generally, the properties of the inner section (e.g. its rigidity or its stiffness) can be adjusted, e.g., by the arrangement of folds, by cuts (preferably already provided in the original sheet of the basic structure) or by connections between facing areas of sheet parts of the inner section. For example, by means of connection areas, the inner section can be presented as an essentially closed body located in the outer section, which is accessible via an open end or base side of the outer section.

Generally, the inner section functions as a grasping support, which facilitates the handling of the surgical implant according to the invention during surgery. The implant can be easily grasped at the inner section by means of a grasping instrument and placed and positioned in the defect to be repaired. Because of the shape of the implant and supported by optional additional strengthening elements (see below) or by the arrangement of connection areas (see above), the implant is well protected from the tip of the grasping instrument penetrating the implant. Moreover, the inner section acts as a filler for filling the defect.

In advantageous embodiments of the invention, the basic structure comprises a mesh. The basic structure can also comprise a composite structure, in which at least one additional layer is added to the mesh, e.g. a film.

The mesh of the basic structure is preferably macroporous with typical pore dimensions of greater than 0.5 mm, which supports good tissue integration. Other pore sizes are conceivable as well, however. The mesh can be provided in any kind known in the art, e.g., warp-knitted or weft-knitted or crochet-knitted or woven. A design as perforated film or foil is also conceivable. Any filaments of the mesh may be bio-absorbable or non-absorbable, depending on the material. The filaments can be designed as mono-filaments or as multi-filaments. Tape yarns and drawn film tapes are conceivable as well. Any blends, mixtures or composites of materials and designs are also possible. Moreover, the filaments can be coated.

Examples for non-absorbable materials are polypropylene ("Prolene") as well as blends of polyvinylidene fluoride and copolymers of vinylidene fluoride and hexafluoropropene ("Pronova"). Examples for absorbable materials are copolymers of glycolide and lactide (in particular in the ratio 90:10, "Vicryl"), poly-p-dioxanone ("PDS"), and copolymers of glycolide and ε-caprolactone ("Monocryl"). The indicated designations are trademarks used by the applicant. Other materials suitable for the use with surgical implants are known in the art as well.

Examples for meshes comprised in the basic structure are "Vypro" and "Vypro II" meshes (containing multifilaments of "Vicryl" and polypropylene), "Ultrapro" meshes (containing monofilaments of "Monocryl" and polypropylene) and soft "Prolene" meshes (containing polypropylene). Again, the indicated designations are trademarks used by the applicant.

As already mentioned, one or more additional layers may be added to the mesh to make it a composite structure. The additional layers may include, e.g. bio-absorbable films, non-absorbable films, and/or oxidized regenerated cellulose. By means of a film, e.g., tissue in-growth can be controlled, and a film can serve as a barrier for adhesion and a means for tissue separation. For example, the mesh of the basic structure can be covered from one or both sides with a polymeric film structure, which is absorbable or permanent and can additionally provide a barrier for adhesion.

Examples for meshes having an additional film layer are "Physiomesh" meshes and "Proceed" meshes; these designations are trademarks used by the applicant. If a "Proceed" mesh comprising one layer of oxidized regenerated cellulose (ORC) is used, the ORC layer should be placed on the outer face of the implant, i.e. that face primarily coming into contact with bodily tissue.

In this way, the flexible basic structure can be a mesh or a composite structure, which is provided as a sheet pre-cut to a desired shape. It is conceivable that the material or structure of the sheet varies over the area of the sheet, depending on the location of the area in question in the implant. From this sheet, the outer section and the inner section of the implant are formed.

In advantageous embodiments of the surgical implant according to the invention, at least one reinforcement element is attached to the basic structure and occupies part of the area of the sheet of the basic structure. Such reinforcement elements can strengthen the outer section as well as the inner section.

For example, a reinforcement element can be formed as a film strip or a pattern of film strips of the resorbable material poly-p-dioxanone ("PDS"), which is laminated to the basic structure. Ribs or a pattern of ribs are conceivable as well, wherein a rib is generally less flat than a strip. Preferably, the reinforcement elements are flexible and are attached to the sheet of the basic structure early in the manufacturing process. Another suitable material for reinforcement elements is Polyglecaprone 25 ("Monocryl"). If the reinforcement elements are made from resorbable material, they may disintegrate and leave a more flexible or softer residual implant.

The reinforcement elements strengthen and stiffen the implant where required. Absorbable pre-shaped, concentric bands or radial ribs, for example, can be laminated to one of the faces of the sheet of the basic structure to provide improved resilience plug properties for better matching of the implant to the defect margins. Further, by using reinforcement elements attached to the basic structure, the grasping and handling of the implant with an instrument for placement and positioning can be facilitated. At the same time, the reinforcement elements can also operate as a penetration protection preventing that a surgeon's instrument penetrates through the, e.g., macro-porous mesh of the basic structure, which could lead to injuries of surrounding tissue.

Moreover, the reinforcement elements or at least one of the reinforcement elements may be colored. In this way, the visibility of the whole implant in the area of surgery can be enhanced, the implant can be more easily oriented, and the grasping and general handling of the implant can be facilitated. For example, the center area of the implant can be marked by colored reinforcement elements. A suitable dye is, e.g., D&C violet No. 2.

Generally, the surgical implant according to the invention provides many advantages. It can be produced as a lightweight structure with low foreign body sensation and causing no or little chronic pain, but nevertheless having sufficient strength. During surgery, it requires minimal manipulation of anatomic structures only and, as a rule, no preperitoneal mobilization. Compared to traditional plug techniques (according to Rutkow), little training is required for working with the implant. Implantation tends to be fast and positioning easy. The inner section provides a convenient grasping and handling help for placing and positioning the implant into the defect by means of a surgical instrument, wherein the tip of the instrument is protected from penetrating the implant and causing injury. Generally, the volume of the defect is filled by the implant, which is flexible. Depending on the desired application and the materials used, the implant can be fully or partially bio-degradable.

The surgical implant can be used to repair defects of different sizes. If required, the implant can be configured and adapted to the defect in question, e.g. by trimming the outer section and/or the inner section. It is also possible to fix the implant at the margins of the defect, e.g. by suturing. Generally, the implant can be used in the pre-peritoneal space as well as in the intra-peritoneal space (abdomen). Other possible uses relate to the repair of ventral hernia defects, umbilical and incisional hernia defects, etc.

Some surgeons prefer to place, after inserting the surgical implant described so far into a hernia defect, a piece of a separate surgical mesh on top of the implant or the bodily tissue in the area of the implant, respectively. To this end, a kit is provided which comprises a surgical implant as described before plus a separate surgical mesh, which is adapted to be placed on top of the tissue or muscle wall defect after the surgical implant has been applied. This separate surgical mesh can be pre-shaped to an appropriate size and/or can be trimmed to the desired size, if required. Preferably, the material of the separate surgical mesh is the same as that of a mesh in the basic structure. The separate surgical mesh can also comprise a composite structure.

A method of manufacturing a surgical implant according to the invention has already been indicated. Generally, one double-sheet of a flexible basic structure is provided, and the outer section and the inner section of the implant are formed from that double-sheet.

More specifically, a double-sheet of the basic structure is provided by folding a single-sheet (of a desired shape) of the basic structure about a fold line or, analogously, by overlaying two single-sheets (of desired shape) of the basic structure. This results in two opposite sheet parts defining the inner section in an area adjacent to the fold line and the outer section in an area distant from the fold line, wherein the opposite sheet parts have edge areas facing each other. (Alternatively, the double-sheet could be cut to the desired shape after it has been provided, or partially cut before and partially cut afterwards.) In the outer section, at least part of these edge areas facing each other are connected to each other, preferably by welding, gluing, and/or suturing. If desired, additional areas of the opposite sheet parts facing each other can be connected to each other as well, again preferably by welding, gluing, and/or suturing. Thereafter, in the outer section, the double-sheet of the basic structure is inverted so that it accommodates the inner section. If the inner section is not automatically accommodated in the outer section when performing the step of inverting, the inner section or parts thereof can be arranged afterwards so that the inner section fits well into the outer section. Reinforcement elements, in particular when strip-like, are preferably attached or laminated to the sheet of the basic structure before folding the sheet about the fold line. Moreover, the basic structure may be provided with incisions or cuts in intermediate steps of the method, which will become more evident from the embodiments described below.

In the following, the invention is described in further detail by means of examples. The drawings show in FIG. 1 in parts (a) to (h) several consecutive steps during the manufacturing of an embodiment of the implant according to the inventing, resulting in the implant shown in part (h) in three-dimensional view, FIG. 2 a first variant of the embodiment according to FIG. 1(h) in three-dimensional view, FIG. 3 a second variant of the embodiment according to FIG. 1(h) in three-dimensional view, and FIG. 4 in parts (a) to (d) several consecutive steps during the manufacturing of another embodiment of the implant according to the inventing, resulting in the implant shown in part (d) in three-dimensional view, and in parts (e) and (f) two three-dimensional views illustrating the use of this implant.

FIGS. 1(a) to 1(h) illustrate a sequence of steps for manufacturing a surgical implant 1 which can be used for repairing a tissue or muscle wall defect.

FIG. 1(a) shows a plan view of a blank of a basic structure 2. This blank is designed as one single sheet 4 having an axis of symmetry A-A. In the finished implant 1, the area adjacent to the axis A-A (on both sides) forms an inner section 6 of the implant 1, whereas the area distant from the axis A-A (on both sides) forms an outer section 8.

In the transition region between the portions of the sheet 4 for defining the inner section 6 and the outer section 8, there are cut-outs 10 and slots 11. In other words, the sheet 4 of the basic structure 2 has been pre-cut to a desired shape, e.g. by laser-cutting or by punching or blanking or by cut-plotting.

In the embodiment, the basic structure 2 comprises a surgical mesh having coarse pores and including monofilaments of "Monocryl" (see above) and polypropylene. Meshes made of such material are marketed by the applicant under the trade name "Ultrapro". Optionally, one side of the mesh may be coated with a layer of oxidized regenerated cellulose.

In a separate step, reinforcement elements formed as a contiguous arrangement of reinforcement strips 12 are prepared, see FIG. 1(b). In the embodiment, the reinforcement strips 12 are cut out from a poly-p-dioxanon film (dyed with D&C violet No. 2) by cut-plotting. This material is absorbable. The reinforcement strips 12 are significantly stiffer than the basic structure 2.

In the step illustrated in FIG. 1(c), the reinforcement strips 12 are laminated to the sheet 4 of the basic structure 2, e.g. by welding.

In the next step, the single sheet 4 including the reinforcement strips 12 is folded about the axis of symmetry A-A, thus forming a double-sheet 14, as shown in FIG. 1(d). In the embodiment, the reinforcement strips 12 are at the inner side of the double-sheet 14 (but they could also be located at the outer side). In this way, the inner section 6 of the implant 1 is defined by two opposite sheet parts of the basic structure 2, i.e. in the area adjacent to the axis A-A at the lower edge 16 of the double-sheet 14. In a similar way, the outer section 8 of the implant 1 is defined by two opposite sheet parts of the basic structure 2, i.e. in the area distant from the lower edge 16.

In the next step, which is shown in FIG. 1(e), edge areas 18 of the sheet parts of the double-sheet 14 facing each other are connected to each other, e.g. by welding. In FIG. 1(e), these edge areas are indicated as shaded areas.

FIG. 1(f) is a three-dimensional view of the resulting double-sheet 14. As additional steps, a cut 20 is cut, which penetrates both parts of the double-sheet 14; alternatively, corresponding cuts could already be provided at the single sheet 4 before the folding step is performed. Moreover, the lower edge 16 of the double-sheet 14 is cut away. In this state, the parts of the double-sheet 14 are held together by the connected edge areas 18.

FIG. 1(g) illustrates how the portion of the double-sheet 14 forming the inner section 6 of the implant 1 is accordion-folded.

In the last step, which is shown in FIG. 1(h), the double-sheet 14 is inverted in the outer section 8. This step can be easily performed, because the basic structure 2 is flexible, and may be facilitated by the presence of the cuts 20. If the inner section 6, which forms an accordion-folded filler, is not automatically accommodated after the outer section 8 has been inverted, it has to be re-arranged so that it well fits into the outer section 8.

Figure 1:
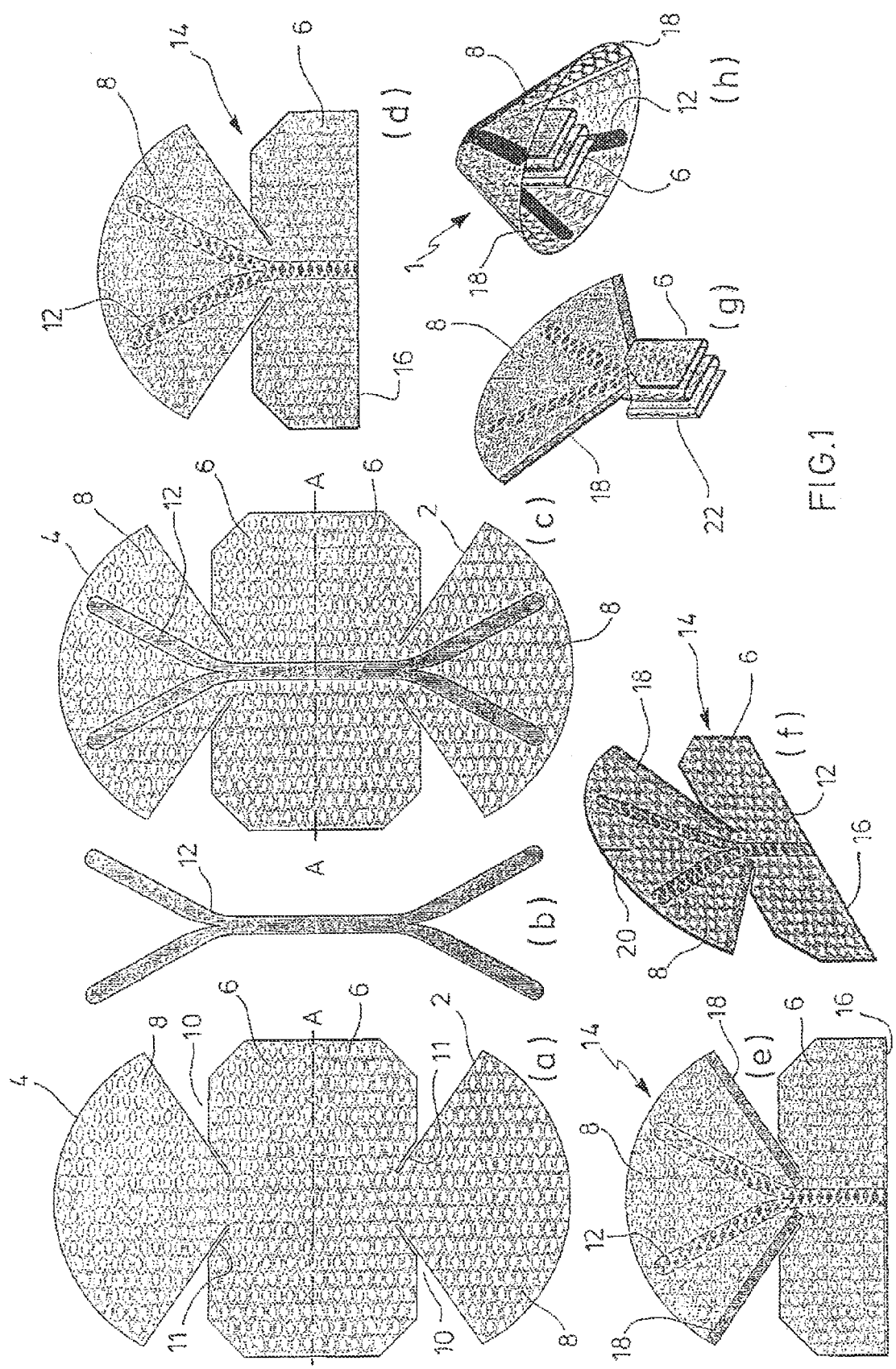

FIG. 1(*h*) shows the implant 1 in its finished state. It comprises an outer section 8 having essentially the shape of the lateral area of a cone (with a rounded tip) and including a flexible mesh material reinforced by the reinforcement strips 12, as well as an inner section 6 made of the same material and having the function of a filler. Since the implant 1 is flexible, it can be easily inserted into a tissue or muscle wall defect, as further illustrated by means of FIG. 4 in the context of another embodiment.

Figure 2:
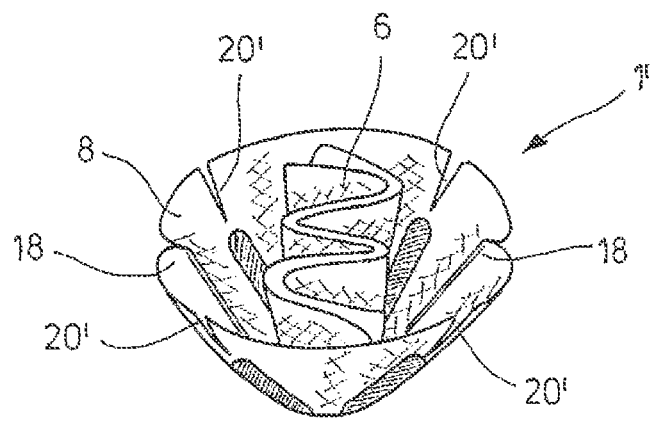

FIG. 2 illustrates a first variant of the embodiment according to FIG. 1(*h*) in three-dimensional view. This variant, designated by 1', is very similar to the implant 1. Instead of the two cuts 20 in FIG. 1(*h*), however, there is provided a total of four cut-outs 20'. Generally, the cuts 20 or the cutouts 20' increase the flexibility of the implant and may facilitate the step of inverting the outer section 8. Embodiments without such cuts are conceivable as well, however.

Figure 3:
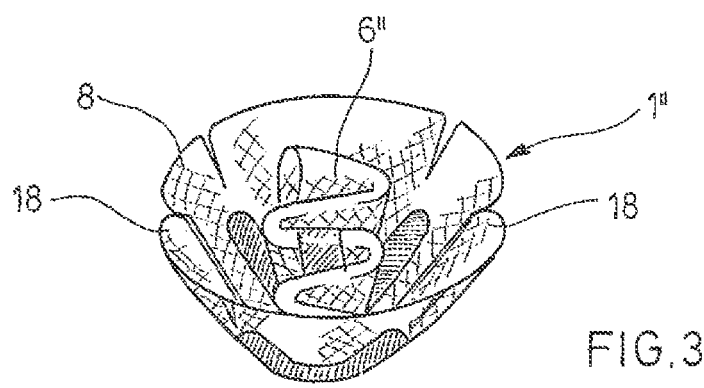

A second variant of the embodiment according to FIG. 1(*h*) is shown in FIG. 3. This variant, designated by 1", is almost identical to the implant 1' of FIG. 2. In contrast thereto, however, the lower edge 16 in FIG. 1(*e*) is not cut away, as in the step according to FIG. 1(*f*). This results in a less open inner section 6" of the implant 1" so that the filler provided by the inner section 6" is generally stiffer.

FIG. 4 shows another embodiment of the surgical implant, which is designated by 30, and also illustrates how the implant 30 is handled during a surgical operation.

The implant 30 comprises a basic structure 32 provided as a blank formed as a single pre-cut sheet, which is shown in FIG. 4(*a*) in a three-dimensional view. This sheet comprises two cut-out areas 34 and an axis of symmetry B-B. Moreover, a reinforcement strip 36 is laminated to one side of the blank.

In manufacturing steps indicated in FIG. 4(*b*), the blank is folded about the axis B-B to provide a double-sheet 38, and edge areas 40 facing each other are connected to each other, e.g. by welding, suturing or gluing. In this way, an inner section 42 and an outer section 44 of the implant 30 are formed. Moreover, in an inner connection area 41 in the border region between the inner section 42 and the outer section 44, the facing sheets are connected to each other as well.

In the step illustrated in FIG. 4(*c*), the outer section 44 is inverted or "rolled up" until it accommodates the inner section 42, which results in the finished implant 30 according to FIG. 4(*d*).

The shape of the outer section 44 of the finished implant 30 is cone-like with a somewhat rounded tip 46, which minimizes the irritation of, e.g., the peritoneum when the implant is inserted. The outer section 42 is stiffened by the reinforcement strip 36 and also by the connected edge areas 40. Generally, however, the implant is rather flexible. By having the reinforcement strip 36 laminated on the basic structure 32, the resilience of the implant 30 will be improved, and the implant 30 is snuggling better to the defect margins. In order to further improve the matching of the implant 30 to the defect margins, additional cuts can be provided on the outer section 44, similar to the cuts 20 or the cut-outs 20'.

FIG. 4(*e*) illustrates how the implant 30 is handled during surgery. The inner section 42 can be easily grasped with a surgical grasping instrument 48. The amount of material of the inner section 42, the presence of the connection area 41 as well as the reinforcement strip 36 prevent the tip of the grasping instrument 48 from penetrating through the generally soft and coarse-pored material of the basic structure 32 and causing injury. FIG. 4(*f*) shows the tip area 46 of the implant 30 with the grasping instrument 48 inserted and the implant 30 somewhat stretched, but the grasping instrument does not puncture the implant 30.

The implant 30 can be inserted into a tissue or muscle wall defect, in particular for repairing a hernia, with the area of the tip 46 ahead. Due to its flexibility, the implant 30 well adjusts to the size and shape of the defect, wherein the inner section 42 serves as a filler. If required, the outer section 44 and the inner section 42 can be trimmed to a desired size, preferably just before inserting the implant 30. Moreover, the edge area of the outer section 44 can be sutured to the bodily tissue, depending on the conditions in the area of surgery.

In the embodiment, the basic structure 32 comprises a surgical mesh of type "Vypro" (see above) including multifilaments of "Vicryl" (see above; absorbable) and polypropylene (non-absorbable). The reinforcement strip 36 is based on "Monocryl". An additional layer, e.g. of oxidized regenerated cellulose, may be added to the mesh, either on one side or on both sides. See also the general remarks further above.

In a variant of the implant 30, there are no reinforcement elements like the reinforcement strip 36.

In another variant, the implant does not involve a folded single sheet, but starts from a double-sheet comprising an overlay of two single sheets. To this end, two pre-cut single sheets are placed on top of each other, which results in a state like that shown in FIG. 4(*b*), but without the two single sheets being connected at the axis B-B of FIG. 4(*a*). Since the sheets are connected in the areas 40 and 41, the manufacturing step according to FIG. 4(*c*) can be performed in the same way as before. In the resulting implant, the inner section is more open, like in the embodiment according to FIG. 2.

Many other embodiments of the implant are conceivable as well. For example, the strengthening elements like strengthening strips or ribs can be arranged in a different pattern (which influences the resilience properties of the implant), or there are no strengthening elements at all. Or, e.g., the shape of the basic structure is not provided via pre-cut single sheets, but the double-sheet obtained after folding one single sheet (which is, e.g. rectangular) or overlaying two single sheets (which are, e.g., rectangular) is cut to the desired shape. The choice of materials has already been generally discussed further above.

The invention claimed is:

1. A surgical implant adapted for repairing a tissue or muscle wall defect, comprising an outer section and an inner section located in the outer section, characterized in that the outer section and the inner section are formed from one double-sheet of a flexible basic structure, wherein the outer section has a generally conical-like or generally frustoconical-like form, wherein the inner section does not have a generally conical-like or generally frustoconical-like form, wherein the inner section is accessible via an open base side of the generally tapered form of the outer section and, wherein the double-sheet of the basic structure comprises a single-sheet folded about a fold line, said fold line being a symmetry axis, resulting in two opposite sheet parts defining the inner section in an area adjacent to the fold line and the outer section in an area distant from the fold line and having edge areas facing each other in the outer section, at least part of said edge areas facing each other are connected to each other.

2. A surgical implant according to claim 1 characterized in that the two opposite sheet parts have cut-outs in a transition region between the inner section and the outer section.

3. A surgical implant according to claim 2, characterized in that, in the inner section, the folded sheet of the basic structure is accordion-folded.

4. A surgical implant according to claim 1 characterized in that the basic structure comprises a mesh.

5. A surgical implant according to claim 4, characterized in that the mesh comprises filaments selected from the group consisting of bio-absorbable filaments, non-absorbable filaments, mono-filaments, multi-filaments, and combinations thereof.

6. A surgical implant according to claim 4 characterized in that the mesh comprises at least one material selected from the group consisting of polypropylene, poly-p-dioxanone, copolymers of glycolide and lactide, copolymers of glycolide and lactide in the ratio 90:10, copolymers of glycolide and ε-caprolactone, and blends of polyvinylidene fluoride and copolymers of vinylidene fluoride and hexafluoropropene.

7. A surgical implant according to claim 4, characterized in that the basic structure comprises a composite structure, in which at least one additional layer is added to the mesh.

8. A surgical implant according to claim 7, characterized in that the at least one additional layer comprises a film.

9. A surgical implant according to claim 8, characterized in that the film has at least one property selected from the group consisting of bio-absorbable, non-absorbable, and comprising oxidized regenerated cellulose.

10. The surgical implant of claim 4, wherein the mesh has a structure selected from the group consisting of macroporous, warp-knit, weft-knit, crochet-knit, woven fabric, and perforated film.

11. A surgical implant according to claim 1 additionally comprising at least one reinforcement element attached to the basic structure and occupying part of the area of the sheet of the basic structure.

12. A surgical implant according to claim 11, characterized in that the at least one reinforcement element comprises at least one of the properties selected from the group consisting of: made as a film, formed as a strip, formed as a rib, laminated to the basic structure, made from poly-p-dioxanone, made from a copolymer of glycolide and ε-caprolactone, and colored.

13. A method of manufacturing a surgical implant having the features of claim 1, characterized by providing one double-sheet of a flexible basic structure and forming the outer section and the inner section from said double-sheet.

14. A method of manufacturing a surgical implant of claim 1, comprising the steps of
providing a double-sheet of the basic structure by folding a single-sheet of the basic structure about a fold line or, analogously, by overlaying two single-sheets of the basic structure, which results in two opposite sheet parts defining the inner section in an area adjacent to the fold line and the outer section in an area distant from the fold line, wherein the opposite sheet parts have edge areas facing each other;
in the outer section, connecting at least part of said edge areas facing each other to each other, preferably by welding, gluing, and/or suturing;
connecting additional areas of the opposite sheet parts facing each other to each other, by welding, gluing, and/or suturing;
in the outer section, inverting the double-sheet of the basic structure so that it accommodates the inner section; and,
arranging the inner section so that it fits into the outer section.

\* \* \* \* \*